(12) United States Patent
Culha

(10) Patent No.: US 8,835,128 B2
(45) Date of Patent: Sep. 16, 2014

(54) IDENTIFICATION METHOD BASED ON SURFACE-ENHANCED RAMAN SCATTERING

(75) Inventor: Mustafa Culha, Istanbul (TR)

(73) Assignee: Yeditepe Universitesi, Istanbul (TR)

( * ) Notice: Subject to any disclaimer, the term of this patent is extended or adjusted under 35 U.S.C. 154(b) by 901 days.

(21) Appl. No.: 12/111,951

(22) Filed: Apr. 29, 2008

(65) Prior Publication Data

US 2008/0268493 A1  Oct. 30, 2008

(30) Foreign Application Priority Data

Apr. 30, 2007 (TR) ............... a 2007 02886

(51) Int. Cl.
*C12Q 1/04* (2006.01)
*G01N 21/65* (2006.01)
*B82Y 15/00* (2011.01)

(52) U.S. Cl.
CPC .......... *C12Q 1/04* (2013.01); *G01N 21/658* (2013.01); *B82Y 15/00* (2013.01)
USPC .......................................... 435/34

(58) Field of Classification Search
None
See application file for complete search history.

(56) References Cited

PUBLICATIONS

Zeiri et al. J. Raman Spectrosc. 2005; 36: 667-675.*

* cited by examiner

*Primary Examiner* — Chris R Tate
*Assistant Examiner* — Douglas F White
(74) *Attorney, Agent, or Firm* — Venable, Campillo, Logan & Meaney PC

(57) ABSTRACT

This invention is related to a reproducible identification method based on surface-enhanced Raman scattering (SERS), in which bacterial samples are used in identification of bacteria by mixing with the concentrated silver and gold nanoparticles.

1 Claim, 1 Drawing Sheet

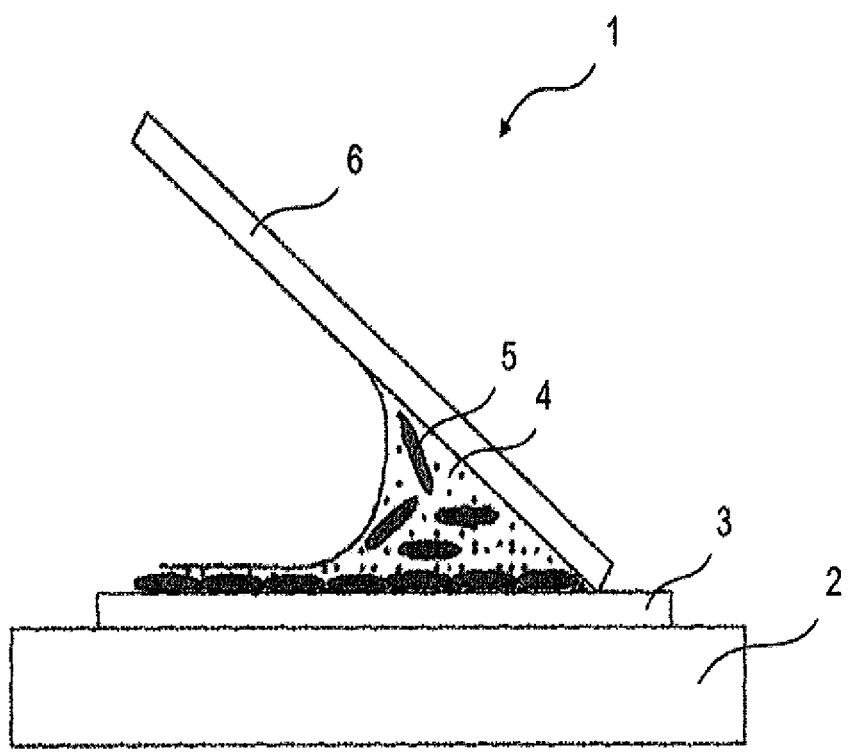

IDENTIFICATION METHOD BASED ON SURFACE-ENHANCED RAMAN SCATTERING

FIELD OF THE INVENTION

This invention is related to sample preparation methods that involve the utilization of the simple mixing of concentrated colloidal silver or gold nanoparticles with bacterial samples to generate a sample, which a laser beam can be directed to proper locations, and the "convective assembly" of bacteria cells and silver or gold nanoparticles to generate a uniform sample for reproducible surface-enhanced Raman scattering (SERS) spectra, which can be used for bacterial identification.

PRIOR ART

The techniques used for microorganism identification can be classified into two groups; genotypic and phenotypic. Biotyping, antibiotic susceptibility, phage typing, serotyping, polyacrylamide gel electrophoresis (PAGE), multilocus enzyme electrophoresis (MLEE) may be given as the examples of phenotypic methods and plasmid profiling, chromosomal DNA profiles and polymerase chain reaction (PCR) based methods can be given as the examples of genotypic methods. Identification and characterization with these methods are expensive, laborious and time consuming. Among these methods, the PCR based methods are highly sensitive and accurate identification based on 16S ribosomal RNA gene of the microorganism can be conducted with the help of said method. In recent years, with the development of real-time PCR apparatus, its usage in identification of microorganisms has become much more efficient and faster. However, it is required that genetic codes of each microorganism be decoded and their primers be prepared in order to develop accordingly identification methods based on PCR. In addition, for the target microorganism whose amplification will be made with PCR to be lysed, its DNA is required to be isolated from the polluted environment in which it is present. It is disputable whether it is suitable for automation and for identification of more than one microorganism simultaneously. Furthermore, PCR based techniques provide almost no information about the morphology, number and cellular environment of the microorganism. In recent years, test-kits based on more developed molecular biology techniques have also been prepared; however, they are still quite expensive and a test-kit is needed for each microorganism. Moreover, automatic systems based on gas chromatography and protein electrophoresis have also been developed, but, preparation step of the microorganism samples takes long time and during extraction, for example, causes sample manipulation.

One of the other methods followed for identification and characterization of microorganisms is the use of the spectroscopic techniques. The first group of these techniques is the matrix assisted laser desorption ionization-time of flight (MALDI-TOF) mass spectroscopy and pyrolysis mass spectroscopy (PyMS). As both of these techniques destruct the microorganism to be identified, it jeopardizes further analysis intended to be conducted, in case the number of microorganism samples is limited. Besides, both of these methods require expensive equipments and highly experienced personnel. The vibrational spectroscopic techniques, particularly IR and Raman can be given as examples for the second group. The vibrational spectroscopic techniques are progressing as the candidate techniques to solve various problems confronted in the area with the help of its abovementioned characteristics for identification and characterization of microorganisms, such as sensitivity, speed, strain level identification, minimal sample preparation, identification even at single microorganism level, and its suitability for automation.

Due to their fingerprinting properties, IR and Raman spectroscopies can provide specific information, for example about the chemical structure of a molecule in a very short time. Raman spectroscopy is a spectroscopy branch related to inelastic scattering of photons, which are used to stimulate the molecule, from the vibrating molecules. Each molecule provides a unique Raman spectrum, which has the finger print characteristic for the same molecule. The obtained spectrum provides very significant information about chemical structure of the molecule. Although IR and Raman spectroscopies are defined as complementary methods, their signal generation processes are essentially different. While IR bands are the result of the change in dipolmoment of a molecule, Raman bands are the result of the change in polarity of the molecule. When these IR and Raman spectroscopic methods are compared, Raman spectroscopy provides significant advantages for studying large biological molecules and molecular structures due to being almost immune to water in the sample and the difference in selection rules over IR. There must be a change in the polarity of electron cloud around the vibrating atom nucleus in order for a molecular vibration to generate a Raman band. Thus, Raman bands of groups such as C=O, C=N, C=C, S—S, S—C, S—H groups, which are bound by more than one bond and are rich in electrons, are stronger than the groups such as C—H and N—H, which are bound by a single bond and are poor in electrons. For example, Raman spectrum of a protein is essentially composed of main peptide chain, aromatic side chain bands containing sulfur. However, in IR spectroscopy, increase in the absorbance of bands is the change in "dipole moment" of vibrating bonds. Thus, spectra of large molecules and molecular structures, such as proteins and nucleic acids are very complicated due to the fact that bands of many sub-structures overlap. Therefore, Raman spectrum is much more simple and easier to explain and to understand when compared to IR spectrum.

Microorganisms, like all biological structures, are composed of various biological molecular structures such as nucleic acids, proteins, carbohydrates and lipids and many other small molecules and ions. A Raman spectrum of a biological structure or microorganism consists of all molecules composing of the same molecular structure or microorganism. As the structure and concentration of the bio and external molecules composing each bio-molecular structure or microorganism are different, spectra obtained from the said structures will be different. With Raman spectroscopy, it is possible to obtain a spectrum having the fingerprint characteristic specific to each microorganism. The developments in IR spectroscopy have reached a level to be used in identification of microorganisms and a system based on IR spectroscopy has been introduced to the market to be used for identification of some important microorganisms (Bruker, Germany). Because scattering of Raman is not affected from water band and its spectrum is more understandable and clear, there has been a significant increase in the recent years in applications of Raman spectroscopy in the field of biology and medicine. Hence, in this context, it will not be wrong to estimate that this method will be an indispensable part of medicinal and test laboratories in the following years.

Although Raman spectroscopy provides significant advantages over IR, it suffers from the weak scattering. In order to remedy this deficiency, surface-enhanced Raman scattering (SERS) was introduced. Since its discovery, it has been proven to a powerful technique for the characterization and investigation of biological molecules and structures. In SERS, gold or silver nanoparticles or surfaces are brought into contact with the molecule or structure in order to enhance the Raman scattering. Although its feasibility is foreseen for fast microorganism detection, the technique suffers from irreproducibility of spectra obtained from bacterial samples. The approach presented here solves the problem of irreproducibility of SERS spectra of bacteria.

BRIEF DESCRIPTION OF INVENTION

The objective of this invention is to develop an identification method by which identification of bacteria will be performed in the shortest time possible with very low costs.

The objective of this invention is related to a SERS based identification method, in which bacteria samples are mixed with concentrated silver and gold nanoparticles and wherein finger print spectra of bacteria belonging to different species and strains obtained from the samples acquired by preparation of mixture as well-ordered structures on a flat surface via a method called convective assembly are obtained in a highly repeatable manner, and used in bacterial identification.

EXPLANATION OF DISCOVERY

The goal of this discovery is rapid and cost effective identification of bacteria.

This discovery resolves the problem of irreproducibility of SERS spectra of bacteria by simple mixing of concentrated silver or gold nanoparticles and depositing the mixture onto a glass slide surface with "convective-assembly" method. The acquired SERS spectra can be used for fast bacterial identification at species and strain level with a single SERS spectrum obtained from the sample.

DETAILED DESCRIPTION OF INVENTION

The convective assembly used in the method realized to attain the object of the invention is shown in the accompanying drawing.
FIG. 1 shows schematic view of the convective assembly.
The parts seen in the FIGURE are each given a reference numeral as follows.
1. Convective assembly
2. Moving stage
3. Glass with hydrophilic surface placed on the moving stage
4. Silver particles
5. Bacteria cells
6. Glass placed with an angle In order to get a SERS spectrum, silver or gold nanoparticles (4) must be in contact.

A Raman microscopy system is used which is composed by adding a microscope to a Raman spectrometer. The microscope is used to focus the coming laser light by intensifying the same. The diameter of a light coming out of the laser depends on the type of laser and wave length, and is about 100 µm. The light which reaches the microscope can be intensively focused depending on the objective used. In this study, a 40× objective is used and the diameter of laser light (830 nm wavelength laser) emerging from the objective is estimated to be about 3 µm. It has been estimated that a light of 3 µm diameter is only able to hit a few bacterial cells and some silver nanoparticles surrounding the bacterial cells. It is assumed that the average diameter of a bacterial cell (5) is about 1 µm.

Previously, spectra obtained from the prepared sample, in which the silver nanoparticles (4) were synthesized and also were simply mixed with the bacterial cells showed significant differences although they were taken from the same sample. Therefore, multiple spectra (in the range of 50-100) were required to be evaluated by statistical methods in order for the said technique to be used. Thereby, identification procedure was lengthened and reliability of the obtained results decreased.

Identification method realized to attain the objective of this invention comprises the following steps;
  Concentrated silver and gold nanoparticles (4) being mixed with bacterial samples (5),
  Silver nanoparticles (5) with an increased concentration causing aggregation, and coming into a better resonance with a laser light in wavelength in the used NIR region,
  A laser radiation used at 830 nm (in NIR region) wavelength preventing fluorescence radiation that might come from bacterial cells (4) and penetrating deeper into the sample,
  Aggregated silver nanoparticles (5) becoming visible in white light by means of surface plasmons under a light microscope objective, and realizing where the laser light will be directed on the sample,
  Thereby the possibility of existence of bacterial cells of the silver nanoparticles with an increased concentration and nanoparticles under the laser light at the same time increasing and reproducibility of the spectra obtained thus being maintained and all the spectra taken from a sample being the same at any time or showing very little variation Another embodiment of the identification method comprises the following steps;
  Silver and bacterial cells being mixed in a certain ratio and laid on a flat surface as a thin layer by means of a method called "convective assembly",
  Convective assembly allowing the mixed silver and bacteria particles to spread over the surface in a great order due to capillary effect during evaporation of the water in the mixture,
  During the settlement process, nanoparticles which are much smaller than the bacterial cells filling within the gaps by entering between the coexisting bacterial cells and forming a well ordered structure,
  As the structure is the same in all parts, the obtained spectrum being specific to the sample and all the spectra taken from the same sample being the same with each other, wherever the laser radiation that hits such a well ordered structure strikes on the sample,
  As it is intended to prepare a standard sample, differences from sample to sample due to preparation of the samples being minimized in this way,
  As nanoparticles are in contact with the bacterial cell at almost all points, the technique allows obtaining a richer or improved spectrum from bacterial cell surface.

In convective assembly (1), on a hydrophilic surface fixed on a moving stage (2), the prepared bacteria-silver nanoparticles mixture is placed at the contact point of a slide (3), on which the hydroxyl groups on the surface are activated and whose surface is cleaned at molecular level, with another slide (6) which is placed and fixed at an angle of 20-24°. After the placement process, the slide (3) above the stage is moved at a certain speed (0.21-2.0 µm/s) by means of the moving stage (2). During said movement, because of the evaporation of water in the mixture and the capillary effect, the bacterial cells (5) and silver nanoparticles (4) are assembled into an ordered structure.

The invention claimed is:

1. An identification method comprising the steps of

Silver nanoparticles (4) and bacterial cells (5) being mixed in a certain ratio in an aqueous medium, placing the prepared bacteria-silver nanoparticles mixture, in a convective assembly set-up (1), on a hydrophilic surface fixed on a moving stage (2), at the contact point of a slide (3), on which the hydroxyl groups on the surface are activated and whose surface has been cleaned at the molecular level, with another slide (6) which is placed at an angle of 20-24°, moving the slide (3) above the stage (2) at a certain speed (0.21-2.0 μm/s) by means of the moving stage (2), the bacterial cells (5) and silver nanoparticles (4) disperse on the slide (3) surface in an ordered structure due to the evaporation of water from the mixture and the capillary effect during the said movement, the silver nanoparticles (4), which are much smaller than the bacterial cells (5), aggregate within the voids among the bacterial cells (5) and forming a well-ordered structure on the way, while the silver nanoparticles (4) and the bacterial cells (5) disperse on the surface, testing of the surface dispersion of the nanoparticles (4) and the bacterial cells (5) formed from the sample by means of analyses of spectra obtained from laser irradiation impinged on the established ordered structure.

* * * * *